United States Patent
Bourne et al.

(10) Patent No.: US 6,195,805 B1
(45) Date of Patent: Mar. 6, 2001

(54) POWDER FREE NEOPRENE SURGICAL GLOVES

(75) Inventors: George Bourne, Libertyville; Theresa A. Moceri, Park City; Yun-Siung Tony Yeh, Libertyville, all of IL (US)

(73) Assignee: Allegiance Corporation, McGaw Park, IL (US)

( * ) Notice: Subject to any disclaimer, the term of this patent is extended or adjusted under 35 U.S.C. 154(b) by 0 days.

(21) Appl. No.: 09/032,632

(22) Filed: Feb. 27, 1998

(51) Int. Cl.$^7$ .......................... A41D 19/015; C08L 11/02
(52) U.S. Cl. ................. 2/168; 2/16; 2/159; 2/161.7; 428/35.7; 428/36.8
(58) Field of Search ................ 428/35.7, 36.8; 422/22; 2/16, 159, 161.7, 168

(56) References Cited

U.S. PATENT DOCUMENTS

| | | | |
|---|---|---|---|
| 3,955,012 | 5/1976 | Okamura et al. | 427/2 |
| 4,918,317 | 4/1990 | Hess et al. | 250/474.1 |
| 4,983,849 | 1/1991 | Thompson et al. | 250/429.3 |
| 5,084,514 * | 1/1992 | Szczechura et al. | 525/123 |
| 5,290,894 | 3/1994 | Melrose et al. | 526/315 |
| 5,295,978 | 3/1994 | Fan et al. | 604/265 |
| 5,300,059 | 4/1994 | Rubinstein et al. | 604/408 |
| 5,376,400 | 12/1994 | Goldberg et al. | 427/2.24 |
| 5,422,068 | 6/1995 | Shalaby et al. | 422/22 |
| 5,422,074 | 6/1995 | Schmidt | 422/28 |
| 5,558,900 | 9/1996 | Fan et al. | 427/2.28 |
| 5,612,083 | 3/1997 | Haung et al. | 264/233 |
| 5,626,947 | 5/1997 | Hauer et al. | 428/195 |
| 5,637,641 | 6/1997 | Becker et al. | 525/102 |
| 5,661,305 | 8/1997 | Lawrence et al. | 250/397 |
| 5,676,996 | 10/1997 | Wada et al. | 427/212 |
| 5,688,855 | 11/1997 | Stoy et al. | 524/505 |
| 5,700,585 | 12/1997 | Lee | 428/500 |
| 5,702,754 | 12/1997 | Zhong | 427/2.12 |
| 5,881,387 * | 3/1999 | Merovitz et al. | 2/161.7 |

FOREIGN PATENT DOCUMENTS

| | | | |
|---|---|---|---|
| 3930753A | * | 3/1991 | (DE) . |
| 2239247A | * | 7/1993 | (GB) . |
| WO 99/24507 | * | 5/1999 | (WO) . |

OTHER PUBLICATIONS

"Electron–Beam Systems for Medical device Sterilization", L. Ray Calhoun, J. Thomas Allen, Harry L. Shaffer, George M. Sullivan, and C. Brian Williams, Jul./Aug. 1997, Medical Plastics & Biomaterials.

"Neoprene Latex and Its Applications with Emphasis on Manufacture of Dipped Goods" C.H. Gelbert and H.E. Berkheimer, ACS Spring Meeting, Rubber Division, Montreal, Quebec, May 27, 1987.

"Electron Beam Sterilization of Medical Products", dated: 1995, authors: A. Othman, I. Manaf, K. Bahari, K. Dhala, F. Yoshill, H. Tachibana, Y. Watanabe, and K. Yoshida.

"Radiation Resistance for Commercial Plastic and Elastomeric Materials", dated: 1989, author: K. Wundrich.

"Development of Radiation Crosslinked a Polyethylene" Z. Ghazali—Abstract of Othman et al. (1995).

Calhoun et al. Medical Plastics and Biomaterials, Jul./Aug. 1997, pp. 26–31, Aug. 1997.*

* cited by examiner

Primary Examiner—Ellis Robinson
Assistant Examiner—Sandra M. Nolan
(74) Attorney, Agent, or Firm—Andrea L. Wayda; Joseph A. Calvaruso

(57) ABSTRACT

A unique powder-free medical glove fabricated from a neoprene copolymer, and a method of making same is described. The gloves of the invention are easily donned without the use of powdered donning agents and retain their puncture resistance, tensile strength, stress at 500% and elongation to break after post-processing by chlorination and sterilization by irradiation. Additionally, the gloves of the invention exhibit minimal discoloration (as measured by the per cent change in yellowness index) and minimal stickiness to themselves and to glove packing materials after sterilization by irradiation.

11 Claims, No Drawings

POWDER FREE NEOPRENE SURGICAL GLOVES

This invention relates to gloves and their manufacture. More particularly, the invention relates to a unique powder-free medical glove fabricated from a neoprene copolymer, and method of making same. The gloves of the invention are easily donned without the use of powdered donning agents and retain their puncture resistance, tensile strength, stress at 500% and elongation to break after post-processing by chlorination and sterilization by irradiation. Additionally, the gloves of the invention exhibit minimal discoloration and minimal stickiness to themselves and to glove packing materials after sterilization by irradiation.

BACKGROUND OF THE INVENTION

Many of the elastomeric materials commonly employed in the manufacture of surgeon's gloves and related articles, such as natural rubber latex, have been said to have allergenic properties. Attempts to render natural rubber gloves hypoallergenic have variously focussed on laminating or coating the interior surface of the glove with a less potentially allergenic material. These laminates and coatings have also been used to improve the wet and dry donning characteristics of the gloves. However, these laminates or coatings can easily crack, especially when the glove is flexed or stretched, and expose the wearer to the base natural rubber polymer used to construct the glove.

An alternative solution to the potential allergenicity problem associated with natural rubber gloves is to eliminate the natural rubber completely and construct the glove from a synthetic elastomer which does not contain potential allergens. However, heretofore known synthetic elastomer gloves have a different feel than natural rubber gloves and are often perceived by the wearer to be less comfortable than natural rubber gloves.

Gloves fabricated from synthetic elastomers can also be difficult to don. Wet and dry donning of gloves can be facilitated by coating the interior of the glove with powder. However, powdered medical gloves increase the risk of contamination and inflammation to the patient if powder from the surgeon's gloves is accidentally introduced into a wound or incision. Powdered gloves are also disfavored in electrical applications because powder is a potential contaminant source in demanding electronic fabrication facilities.

SUMMARY OF THE INVENTION

The present invention provides a powder-free glove fabricated from a synthetic elastomer wherein good donning characteristics are obtained without the need for powdered donning agents such as talc, corn starch or calcium carbonate and without the need to provide a continuous polymeric laminate or coating on the interior surface of the glove.

The present invention also provides a powder-free synthetic elastomer glove which possesses various physical properties such as puncture resistance, tensile strength, stress at 500% and elongation to break that are comparable to those exhibited by natural rubber gloves yet which are free of proteins and other potential allergens.

The present invention further provides a powder-free synthetic elastomer glove which, after post-processing by chlorination and sterilization by electron beam radiation, retains, and in some cases, enhances its physical properties and exhibits minimal discoloration and minimal stickiness to itself and to the glove packing material.

According to an aspect of the present invention there is provided a powder-free hypoallergenic glove fabricated from a neoprene copolymer which has physical properties such as puncture resistance, tensile strength, stress at 500% and elongation to break that are at least comparable to natural rubber gloves.

According to a further aspect of the invention there is provided a powder-free hypoallergenic glove fabricated from a neoprene copolymer which retains its puncture resistance, tensile strength, stress at 500% and elongation to break after post-processing by chlorination and electron beam sterilzation. Additionally, the glove of the invention exhibits minimal discoloration and minimal stickiness to itself and to the glove packing material after sterilization with electron beam radiation.

According to another aspect of the invention, the neoprene copolymer glove, which may be manufactured using glove manufacturing techniques and processes such as those set forth in "Natural Rubber Dipping Technologies" by R. D. Culp and B. L. Pugh, symposium on Latex as a Barrier Material, Apr. 6 and 7, 1989, University of Maryland, is rendered powder-free by post-processing chlorination and then sterilized by irradiation. Electron beam sterilization produces a glove whose physical properties (such as puncture resistance, tensile strength, stress at 500%, elongation to break, color and stickiness) are superior to gloves sterilized by the more commonly used gamma beam irradiation at the same dose.

PREFERRED EMBODIMENTS OF THE INVENTION

The Neoprene Copolymer Latex

The gloves of the invention are preferably formed from a copolymer latex of neoprene (also known as chloroprene or 2-chloro-1,3-butadiene) and 2,3-dichloro-1,3-butadiene. Preferably, the neoprene/2,3-dichloro-1,3-butadiene copolymer contains between about 25 to about 55% chlorine. More preferably, the copolymer contains between about 35% to about 45% chlorine. In the most preferred embodiment of the invention, the copolymer contains about 40% chlorine. Other suitable monomers which may be copolymerized with neoprene include sulfur, methacrylic acid, acrylonitrile, 2-cyano-1,3-butadiene and 1,1,3-trifluoro-1,3-butadiene.

The modulus of elasticity of the copolymers of the invention should not be greater than about 0.6 MPa at 100% elongation. Preferably, the modulus of elasticity is about 0.4 MPa at 100% elongation. A detailed explanation of these values is set forth in the duPont Bulletin, "A Selection Guide For Neoprene Latexes", Table II, by C. H. Gilbert, 1985 (NL-020.1 (R1)) which is hereby incorporated by reference.

The neoprene copolymers of the invention have a solids content ranging from between about 35% to about 60% by weight. The preferred solids content of the neoprene copolymer is about 50%.

The neoprene copolymers employed in the present invention have a slow crystallization rate, a medium gel content of about 60% and a high wet gel strength. The neoprene copolymer latexes are preferably anionic. Additional information about these polymers is contained in the above-referenced duPont bulletin as well as duPont Bulletin "Neoprene Latexes-Their Preparation And Characteristics", L. L. Harrell, Jr., 1981 (ADH 200.1) which is hereby incorporated by reference.

The most preferred neoprene copolymer latex used in the practice of the invention is a copolymer of neoprene and 2,3-dichloro-1,3-butadiene which is sold commercially by duPont under the code number 750. This anionic copolymer latex has a chlorine content of 40% and possesses the preferred properties disclosed above for the neoprene copolymer. A specific description of this latex appears in the duPont Bulletin authored by Gilbert referenced above.

The neoprene copolymer latex can also be blended with other inorganic fillers such as calcium carbonate, carbon black and clay as well as other elastomers such as nitrile rubber, polyisoprene, styrene butadiene rubber and butyl rubber. These neoprene copolymer blends are particularly suitable for manufacture of industrial, surgical and examination gloves of the invention.

Glove Compounding Ingredients

The compounding agents used in glove formulation are set forth below.

| INGREDIENTS | PARTS PER HUNDRED RUBBER (PHR) |
| --- | --- |
| Neoprene copolymer latex or blend | 100.00 |
| Plasticizer stabilizer | 0.5 to 5.00 |
| Emulsifier stabilizer | 0.5 to 5.00 |
| Antiozonant | 0.25 to 5.00 |
| pH stabilizer sequestrate | 0.10 to 1.50 |
| pH stabilizer | 0.10 to 1.50 |
| Vulcanization activator | 1.0 to 10.00 |
| Crosslinker | 0.50 to 3.0 |
| Vulcanization accelerator | 0.5 to 4.00 |
| Antioxidant | 0.10 to 3.00 |
| White pigment (optional) | 0.05 to 3.00 |
| Yellow pigment (optional) | 0.05 to 3.00 |
| Rubber reodorant (optional) | 0.001 to 1.0 |
| Wetting agent emulsifier | 0.001 to 1.0 |
| Defoamer | 0.001 to 2.0 |
| Rubber softener (optional) | 0.0 to 20.0 |

The plasticizer stabilizer may be, for example, oleates, stearates, caseinates or other non-ionic surfactants. Suitable emulsifier stabilizers comprise sodium alkyl sulfates, potassium salts of resin/rosin acids or other non-ionic and ionic surfactants.

Typical antiozonant used in the present invention include paraffinic waxes, microcrystalline waxes and intermediate types (which are blends of both paraffinic and microcrystalline waxes).

pH stabilizer sequestrate is, for example, sodium silicate. The pH stabilizer may be potassium hydroxide, ammonium hydroxide and/or sodium hydroxide.

Suitable vulcanization activators comprise metal oxides, such as magnesium oxide, lead oxide, preferably zinc oxide. Typical crosslinkers used in the present invention include sulfur or other organic peroxides. Vulcanization accelerator is chosen from mercaptobenzothiazoles and derivatives, dithiocarbamates and derivatives, sulfur donors, guanidines and aldehyde-amine reaction products. The antioxidant may be hindered arylamines or polymeric hindered phenols.

White and yellow pigments are optionally present in the formulation. Typical white pigments that may be used are titanium dioxide or other organic pigments. Typical yellow pigments of utility in the present invention are iron oxide or other organic pigments.

Rubber reodorant is optionally used in the present invention and may include perfume oils.

Suitable wetting agent emulsifiers include non-ionic ethoxylated alkyl phenols such as octylphenoxy polyethoxy-ethanol or other non-ionic wetting agents. Defoamer may be chosen from naphthalene-type defoamers, silicone-type defoamers and other non-hydrocarbon-type defoamers.

Rubber softener is optionally present in the amount 0.00 to 20.00 parts per hundred rubber. Suitable rubber softeners in the present invention include esters, petroleum hydrocarbon oils, adipates, phthalates and oleates.

Those skilled in the art will readily be able to vary the compounding ingredients in the dipping formulation to suit the particular neoprene copolymer used as well as the particular final article desired. It will also be understood by those of skill in the art that the specific chemicals or compounds which have been listed above are intended to be representative of conventional materials that may be used in formulating the neoprene copolymer latex and are merely intended as non-limiting examples of each such component of the formulation.

The neoprene copolymers and formulation mixture prepared in accordance with the invention can be be used to fabricate a variety of rubber articles, including surgical and examination gloves, industrial gloves, finger cots, catheters, tubing, protective coverings, balloons for catheters, condoms and the like. However, the primary focus of the inventive neoprene copolymers and formulations is their use in the manufacture of powder-free gloves and other articles.

The gloves fabricated in accordance with the present invention are prepared as follows. A mold in a contoured shape of a glove is first oven dried and then dipped into an alcohol-based coagulant dispersion comprising methanol, surfactants and calcium carbonate. The coagulant layer deposited on the glove former is air dried. The glove former is then dipped into the neoprene copolymer formulation set forth in Table 1 and a film of the rubber latex is coagulated onto the glove former. While still on the former, the coagulated neoprene copolymer latex is leached with water and then dipped into a powdered slurry containing surfactants, crosslinked corn starch powders, silicone and water. The leached, powdered gloves are then beaded and cured. The gloves are cooled on the formers and then stripped from the mold.

The gloves stripped from the former are powdered on both their exterior and interior surfaces. The glove has a coating of calcium carbonate powder on the outer surface of the glove and a coating of cross-linked corn starch powders on the inner surface of the glove. Powder-free neoprene copolymer gloves are produced by a sequence of post-processing steps comprising manually turning the gloves inside out, prewashing, chlorination, neutralization, rinsing several times with water, lubrication and heating with a lubricant solution such as a mixture of cetylpyridinium chloride and Dow Corning Silicone Antifoam 1920, cooling, manually inverting the gloves inside out followed by several cycles of drying and cooling the gloves.

Other suitable lubricants that may be added to the gloves after chlorination to improve wet donning with respect to skin are nonionic and ionic surfactants. The cationic and amphoteric surfactants are most preferred. These surfactants may also be combined with other lubricants such as silicones, or other water soluble polymers such as chitosan, polyacrylic acid, polyethylene oxide and polyvinyl alcohol to provide the desired donning properties.

After the powder-free neoprene copolymer gloves are cooled, they are sorted into pairs comprising a right and a left hand. A package is formed by packing a pair of gloves in a 40 lb. web paper, which is then placed in a 30 lb. top web paper. Fifty individual glove packages are then placed in a dispenser box and four dispenser boxes are then placed in a case and sent to an outside supplier for sterilization by irradiation.

When the neoprene copolymer or blend is used to fabricate surgical gloves, the gloves of the invention have a thickness of at least about 0.004 inches. Preferably, the thickness of the gloves ranges between about 0.006 inches and about 0.008 inches. Most preferably, the glove thickness is between about 0.007 and about 0.008 inches.

The gloves of the invention exhibit physical properties well-suited to their use as surgical gloves. In particular, the surgical gloves of the invention before ageing have a tensile strength of greater than about 2500 psi, preferably greater than about 2800 psi and most preferably, greater than about 3000 psi. The stress at 500% of the surgical gloves of the invention is less than about 1015 psi, preferably less than about 800 psi and most preferably, less than about 500 psi. The surgical gloves of the invention have an elongation to break greater than about 650%, preferably greater than about 750% and most preferably greater than about 800%. Tensile strength, stress at 500% modulus and elongation to break are measured according to ASTM D412-92.

The surgical gloves of the invention also exhibit a minimal tendency to stick to themselves and to their packing material. This feature makes the gloves easy to don and relatively easy to remove from their packing material. The stickiness of the gloves of the invention is determined by a modification of the ASTM D3354-96 film blocking test as set forth more fully below under "Test Procedures". The stickiness of the surgical gloves of the invention is less than about 0.2 lb., preferably less than about 0.1 lb. and most preferably less than about 0.02 lb.

The surgical gloves of the invention are also minimally discolored where the degree of discoloration is assessed using the yellow index described in ASTM D1925 and E313. The per cent change in the yellowness index of the surgical gloves of the invention after electron beam sterilization is less than about 15% as measured by ASTM D1925 and less than about 10% as measured by E313, preferably less than about 12% as measured by ASTM D1925 and less than about 8% as measured by E313 and most preferably less than about 10% as measured by ASTM D1925 and less than about 6% as measured by E313. The per cent change in yellowness index of the surgical gloves of the invention may vary with the amount and types of pigments used in the formulation and the storage conditions that the test samples have been exposed to.

The puncture resistance of the surgical gloves of the invention is greater than about 2.0 lb., preferably greater than about 2.5 lb. and most preferably greater than about 3.0 lb.

When the neoprene copolymer or blend is used to fabricate sterile and nonsterile examination and industrial gloves, the gloves of the invention have a thickness of at least about 0.003 inches. Preferably, the thickness of the gloves ranges between about 0.004 inches and about 0.007 inches. Most preferably, the glove thickness is between about 0.005 and about 0.007 inches. For examination gloves of the invention, the tensile strength is greater than about 1500 psi, preferably greater than about 2000 psi and most preferably greater than about 2500 psi. The elongation to break of the examination gloves of the invention is greater than about 300%, preferably greater than about 500% and most preferably greater than about 650%. The puncture resistance, stress at 500%, stickiness and per cent change in yellowness index of the sterile and nonsterile examination and industrial gloves of the invention are as set forth above for the surgical gloves of the invention.

The invention is illustrated by the following examples. It is understood that one of ordinary skill in the art will understand how to vary the times and temperatures of the process in accord with the article manufactured, the specific neoprene copolymer or blend employed, the particular formulation ingredients selected and the lubricant added to the gloves after chlorination.

EXAMPLE 1

Sterile powder-free neoprene copolymer gloves were manufactured by first preheating a glove former in an oven maintained at about 100 to about 200° F. The glove former was then dipped into an alcohol-based coagulant dispersion maintained at less than about 110° F. for enough time to allow the coagulant to coat the former. The coagulant dispersion is comprised of 50–70 wt. % methyl alcohol, 25–40 wt. % calcium nitrate and 5–15 wt. % calcium carbonate. 0 to about 0.2% non-ionic wetting agent may be used as required. The coagulant layer which had been deposited on the glove former was then allowed to air dry.

The glove former with the dried coagulant layer was then dipped into the compounded neoprene rubber copolymer latex which was maintained at about 70 to about 85° F. The neoprene copolymer used was a copolymer of chloroprene and 2,3-dichloro-2,3-butadiene obtained from duPont bearing the code number 750. The glove former was left in the latex formulation for enough time to allow the neoprene copolymer rubber latex to coagulate on the glove former to reach the desired thickness. The glove former was then removed from the latex and the coagulated latex was leached for about 5 to about 8 minutes in a water leaching tank maintained at about 100 to about 150° F.

The glove former was then dipped into a powder slurry comprised of 0.02–0.1 wt. % stabilizers, 10–20 wt. % cross-linked corn starch powders, 0.5–1.5 wt. % silicone and water. If required, a small amount of wetting and antimicrobial agents may also be added. The gloves were then beaded using a beader. The gloves were cured while still on the former in an oven at a temperature of about 330° F. for about 20 to about 30 minutes. The gloves were then cooled and stripped from the former.

The gloves stripped from the former have calcium carbonate powders coated on the patient or outer surface of the glove and crosslinked corn starch powders coated on the user or inner surface of the glove. To produce powder-free gloves with acceptable product performance for surgical applications, the powdered gloves manufactured using the above-described process must be subjected to post-processing treatment comprising the steps of turning the gloves inside-out, chlorination, neutralization, rinsing, lubrication and drying as follows.

The powdered gloves manufactured according to the above process were manually turned inside out so that the user or inner surface was on the outside of the glove. The powdered neoprene copolymer gloves were then weighed and 60–80 pounds of the gloves were loaded into the chlorinator where the gloves were prewashed for a few minutes. The gloves were then chlorinated while tumbling at a chlorine flow rate of about 800 to about 1500 lbs chlorine gas/24 hours. The gloves were then neutralized with a solution of base. The gloves were then neutralized a second time. At the end of the two neutralization steps, the pH of the solution should be about 7 or above. The second neutralization solution was then drained from the gloves and the gloves rinsed and tumbled with water.

The gloves were loaded into the washer/extractor. The washer/extractor was then filled with water and the gloves were washed for a few minutes and extracted twice. The gloves were removed from the washer/extractor and loaded into a dryer/lubricator. The gloves were tumbled in the dryer/lubricator while heating at about 95 to about 115° F. for several minutes. The gloves were sprayed with the lubricant solution during heat tumbling wherein the lubricant solution comprised water and 0.5–1.5 wt. % of cetylpyridinium chloride. A small amount of Silicone Antifoam 1920 supplied by Dow Corning may be added if required. The gloves were heat tumbled at about 95 to about 115° F. for about 20 minutes. The gloves were cooled down for about 10 minutes.

The gloves were manually inverted inside out and loaded into a dryer. The gloves were then dried at about 95 to about 115° F. for about 25 to about 45 minutes or until the gloves were completely dried. The gloves were cooled for about an additional 5 minutes. At the end of this cooling period, the gloves were ready for packaging.

The finished gloves were packaged as follows. A pair of powder-free gloves, a right and a left hand, were manually cuffed down about 4 inches so that the inside surface of the cuff was exposed to the outside. The left hand glove was laid flat in the left side of the bottom web paper with the thumb exposed outward and the paper wrapped around the glove. Then, the right hand glove was laid flat in the right side of the bottom web paper with the thumb exposed outward and the paper wrapped around the glove. One wrapped glove was then flipped over the other to produce a rectangular wallet-shaped packet. The bottom web paper with a pair of gloves was then wrapped into a top web paper, packed and heat sealed on all sides. 50 pairs of gloves were packed into a dispenser box and 4 boxes were then packed into a carton.

The finished, packed gloves were then sent to a commercial gamma irradiation facility for sterilization. The gloves were exposed to a minimum radiation dose of 61.3 KGy and a maximum radiation dose of 67.6 KGy. The total irradiation exposure time necessary to accumulate the required dose was estimated at about 5.2 hours.

The procedures and methods employed to irradiate medical devices are described more fully in "Electron-Beam Systems For Medical Device Sterilization", L. Ray Calhoun, J. Thomas Allen, Harry L. Shaffer, George M. Sullivan and C. Brian Williams, Medical Plastics and Biomaterials, July/August 1997, pgs. 26–31 which is hereby incorporated by reference.

The physical properties of the gloves were measured immediately after sterilization and after ageing for 12.5 months at room temperature. Immediately after sterilization, the gloves had a tensile strength of 2888 psi, a stress at 500% of 231 psi and an elongation to break of 914% wherein the sample tested had a gauge of 0.0066 inches. The test results are the means of median values of 13 sample sets of 5 dumbbell samples per set.

TEST PROCEDURES

The puncture resistance, tensile strength, stress at 500%, elongation to break, stickiness and degree of discoloration of the aged gloves are summarized in Table 2. Tensile strength, stress at 500% modulus and elongation to break were measured according to the procedures set forth in ASTM D412-92 and are the median values of 5 dumbbell samples.

The degree of stickiness of the gloves was quantitated using a modification of the ASTM D3354-96 film blocking test wherein the two aluminum blocks used in the modified test measured 3"×4" instead of the 4"×4" test blocks specified in the test procedure. In the modified test, a 3"×4 sample including the bead was cut from the cuff area of the sterile powder-free neoprene copolymer gloves. The resulting sample has four layers with three blocked interfaces wherein two of the interfaces arise from the sticking together of the glove outside surface in the cuff area and in the palm area and the third interface arises from the sticking together of the glove inside surfaces in the palm area. The force required to unblock the interface between the glove outside surfaces was taken to be a representative measure of the stickiness of the glove. The test results represent the average peak load values of the four measurements obtained from a pair of gloves.

The puncture resistance of the gloves was measured according to Australian puncture test OS 215. Both the puncture resistance in the cuff and palm areas of the powder-free gloves was measured. The test results represent the average of 5 replicate samples.

The tendency of the sterile powder-free neoprene copolymer gloves to discolor was assessed using ASTM D1925 and E313. In this test, a sample film measuring approximately 3"×3" was cut from the palm area of the glove, the outside surface of the glove exposed to the light beam and the yellowness indices determined. The higher the yellowness index, the more yellow or discolored the glove. The test results for each example were obtained from one sample film.

EXAMPLE 2

In this example, the manufacture and post-processing of the powder-free neoprene copolymer gloves were the same as for Example 1. The gloves were sterilized with gamma radiation at a different commerical gamma irradiation facility where the minimum dose of gamma irradiation was 68.6 KGy and the maximum dose was 83.0 KGY with an exposure time of 13.2 hours estimated for the accumulation of the required dose.

The physical properties of these gloves were also measured immediately after sterilization and after ageing for 12 months at room temperature. Immediately after sterilization, the gloves had a tensile strength of 2356 psi, a stress at 500% of 236 psi and an elongation to break of 960% wherein the sample tested had a gauge of 0.0067 inches. The puncture resistance, tensile strength, stress at 500%, elongation to break, stickiness and degree of discoloration of the aged gloves are summarized in Table 2.

Surprisingly, gloves prepared according to Example 2 and tested immediately after sterilization failed to pass the ASTM D3577-91 tensile strength specification for surgical gloves. Example 2 gloves with a gauge of 0.0067 inches exhibited a tensile strength of 2356 psi whereas a minimum tensile strength of 2466 psi is required by ASTM D3577-91. Furthermore, in both Examples 1 and 2, gloves sterilized by gamma irradiation were unacceptably discolored and sticky, both to themselves and the glove packing material. Accordingly, an alternative method of sterilization was investigated. Example 3 below sets forth the manufacture of a neoprene copolymer glove and its post-processing chlorination and sterilization by electron beam irradiation.

EXAMPLE 3

Powder-free neoprene copolymer gloves were made by following the manufacture and post-processing steps set forth in Example 1. The packaged gloves were then sterilized with electron beam irradiation at a minimum dose of 29.4 KGys and a maximum radiation dose of 51.3 KGy with an exposure time of 0.3 hours estimated for the accumulation of the required dose. This dose rate is the dose rate necessary to meet the SAL of $10^{-6}$ for these powder-free neoprene copolymer gloves with the specified loading density.

The physical properties of these gloves were measured after ageing for 2.5 months at room temperature. The puncture resistance, tensile strength, stress at 500%, elongation to break, stickiness and degree of discoloration of the aged gloves are summarized in Table 2.

The physical properties of gloves prepared in a comparable manner were also measured immediately after sterilization. These gloves had an average tensile strength of 3346 psi, an average stress at 500% of 385 psi and an average elongation to break of 883% wherein the samples tested had an average gauge of 0.072 inches. The average values reported above are the means of median values of 6 sample sets of 5 dumbbell samples each. The six samples were obtained from 6 different production batches.

powder-free medical glove fabricated from a neoprene copolymer which retains its desirable physical properties and which additionally exhibits minimal stickiness and discoloration after sterilization by electron beam irradiation.

The foregoing description and examples relate only to preferred embodiments of the present invention and numerous changes and modifications may be made therein without departing from the spirit and scope of the invention as defined in the following claims.

What is claimed is:

1. A powder-free glove fabricated from a neoprene copolymer having a tensile strength of at least about 2500 psi, a stress at 500% no greater than about 1015 psi, an elongation to break of at least about 650% and a stickiness no greater than about 0.2 lbs wherein the glove is sterilized by treatment with electron beam radiation.

TABLE 2

| Sample | Gauge (in.) | Tensile Strength (psi) | Stress @ 500% (psi) | Elongation (%) | Puncture Resistance (lbs) Cuff | Puncture Resistance (lbs) Palm | Stickiness (lbs) | Yellowness Index D1925 | Yellowness Index E313 |
|---|---|---|---|---|---|---|---|---|---|
| Example 1 | 0.0066 | 3100 | 750 | 780 | 3.48 | 3.56 | 0.73 | 103.92 | 72.41 |
| Example 2 | 0.0067 | 3000 | 750 | 750 | NA | NA | NA | 107.82 | 74.64 |
| Example 3 | 0.0072 | 3800 | 450 | 880 | 3.26 | 3.34 | 0.02 | 82.38 | 60.56 |

Comparison of the property values for the gamma irradiated neoprene copolymer gloves of Examples 1 and 2 with the electron beam irradiated gloves of Example 3 clearly shows that electron beam sterilization produces gloves that solve the problems associated with gamma irradiation.

The electron beam irradiated neoprene copolymer glove has superior physical properties in comparison to the gamma irradiated neoprene copolymer glove. The tensile strength and elongation to break of the electron beam irradiated gloves is higher than the gamma irradiated gloves and the stress at 500% modulus is lower.

The Example 3 electron beam irradiated gloves easily satisfy the criteria for surgical gloves set forth in ASTM D3577-91. Of particular note is the minimal stickiness and discoloration observed with the electron beam irradiated gloves. Compared to the gamma irradiated gloves of Examples 1 and 2, the electron beam irradiated gloves of Example 3 are much less sticky (by a factor of 35; 0.73 lbs vs. 0.02 lbs). Because of their decreased stickiness, the electron beam sterilized neoprene copolymer gloves do not readily stick to themselves and do not stick to the glove packing material as do the gamma irradiated gloves. Consequently, the electron beam irradiated gloves are easy to don and remove from the packing material.

In contrast, the gamma irradiated gloves are so sticky that they are almost impossible to don. Additionally, the gamma irradiated gloves also adhere much more strongly to the glove packing material making them difficult to remove. Finally, the electron beam irradiated gloves are less yellow than the gamma irradiated gloves.

It will be apparent from the foregoing description and examples that the present invention provides a unique 2. A glove as in claim 1 wherein the neoprene copolymer is a copolymer of chloroprene and 2,3-dichloro-1,3-butadiene.

3. A glove as in claim 2 wherein the glove has a puncture resistance of greater than about 2 lbs.

4. A glove as in claim 3 where the per cent change in the yellowness index measured according to ASTM D1925 is no greater than about 15%.

5. The glove of claim 2 wherein the neoprene copolymer contains between about 25% to about 55% chlorine by weight.

6. The glove of claim 5 wherein the neoprene copolymer contains about 40% chlorine by weight.

7. A powder-free glove fabricated from a neoprene copolymer of chloroprene and 2,3-dichlorobLitacliene blended with an elastomer selected fram the group consisting of nitrile rubber, polyisoprene, styrene butadiene rubber and butyl rubber wherein said glove is sterilized by treatment with electron beam radiation and has a tensile strength of at least about 2500 psi, a stress at 500% no greater than about 1015 psi, an elongation to break of at least about 650% and a stickiness no greater than about 0.2 lbs.

8. The powder-free glove of claim 7 wherein the elastomer is nirile rubber.

9. The powder-free glove of claim 7 wherein the elastomer is polyisoprene.

10. The powder-free glove of claim 7 wherein the elastomer is styrene butadiene rubber.

11. The powder-free glove of claim 7 wherein the elastomer is butyl rubber.

* * * * *